US00PP21954P2

(12) United States Plant Patent
Dean et al.

(10) Patent No.: US PP21,954 P2
(45) Date of Patent: May 31, 2011

(54) ***PHORMIUM* PLANT NAMED 'MOONRAKER'**

(50) Latin Name: ***Phormium cookianum*×*Phormium tenax***
Varietal Denomination: Moonraker

(76) Inventors: Mark Dean, Oropi (NZ); Esme Dean, Oropi (NZ)

( * ) Notice: Subject to any disclaimer, the term of this patent is extended or adjusted under 35 U.S.C. 154(b) by 0 days.

(21) Appl. No.: 12/661,442

(22) Filed: Mar. 17, 2010

(51) Int. Cl.
*A01H 5/00* (2006.01)

(52) U.S. Cl. ..... Plt./373

(58) Field of Classification Search ..... Plt./373
See application file for complete search history.

(56) References Cited

OTHER PUBLICATIONS

Upov Plant Variety database 2010/06 p. 1.*

* cited by examiner

*Primary Examiner* — Annette H Para
(74) *Attorney, Agent, or Firm* — Penny J. Aguirre

(57) ABSTRACT

A new cultivar of hybrid *Phormium* named 'Moonraker' that is characterized by its foliage that is variegated with bright green margins and creamy yellow-green centers, its slightly arching plant habit, its small leaves, and its compact plant habit.

2 Drawing Sheets

Botanical classification: *Phormium cookianum*×*Phormium tenax.*

Cultivar designation: 'Moonraker'.

CROSS REFERENCE TO A RELATED APPLICATION

This application is co-pending with a U.S. Plant patent application filed for a plant derived from similar parentage in the Inventors' breeding program that is entitled *Phormium* Plant Named 'Chocomint' (U.S. Plant Pat. No. 12/661,426).

BACKGROUND OF THE INVENTION

The present invention relates to a new and distinct cultivar of *Phormium* named 'Moonraker', an interspecific hybrid of *Phormium cookianum*×*Phormium tenax* and referred to hereafter by its cultivar name, 'Moonraker'. The new cultivar is grown for use as a foliage plant for landscape and container use.

The Inventors discovered the new cultivar summer of 2001 as a naturally occurring chimeral mutation of *Phormium* 'Yellow Wave' (not patented) in a container block in their nursery in Tauranga, New Zealand.

Asexual reproduction of the new cultivar was first accomplished by division in autumn of 2001 in Tauranga, New Zealand by one of the Inventors. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Moonraker' as a new and unique cultivar of *Phormium.*

1. 'Moonraker' exhibits foliage that is variegated with bright green margins and creamy yellow-green centers.
2. 'Moonraker' exhibits a slightly arching plant habit.

3. 'Moonraker' exhibits leaves that are small in size.
4. 'Moonraker' exhibits a compact plant habit; reaching 40 to 60 cm in height.

'Moonraker' can be compared to the parent plant, 'Yellow Wave'. 'Yellow Wave' is similar to 'Moonraker' in having foliage with variegation that is yellow, green, and cream in color. 'Yellow Wave" differs from 'Moonraker' in that the green coloration of the foliage is darker and less green-yellow, in having leaves that are larger in width and length, and in having a less compact plant habit. The closest comparison cultivar is 'Cream Delight' (not patented), which is similar in having leaves with green and creamy yellow variegation. The foliage of 'Cream Delight' differs from 'Moonraker' in that the green coloration is darker and less green-yellow and the creamy colored centers are less green. 'Cream Delight' also differs from 'Moonraker' in having an arching form typical of *Phormium cookianum* type *Phormium* that arches from the base rather being upright and then arching as observed with 'Moonraker'. 'Chocomint', also a mutation of 'Yellow Wave', differs from 'Moonraker' in having variegated foliage with purple brown centers and green margins.

BRIEF DESCRIPTION OF THE DRAWING

The accompanying colored photographs illustrate the overall appearance and distinct characteristics of the new *Phormium.* The photographs in FIG. 1 and FIG. 2 were taken of a two year-old plant of 'Moonraker' as grown outdoors in a 3-liter container in Auckland, New Zealand.

DETAILED BOTANICAL DESCRIPTION OF THE PLANT

Figure 1:
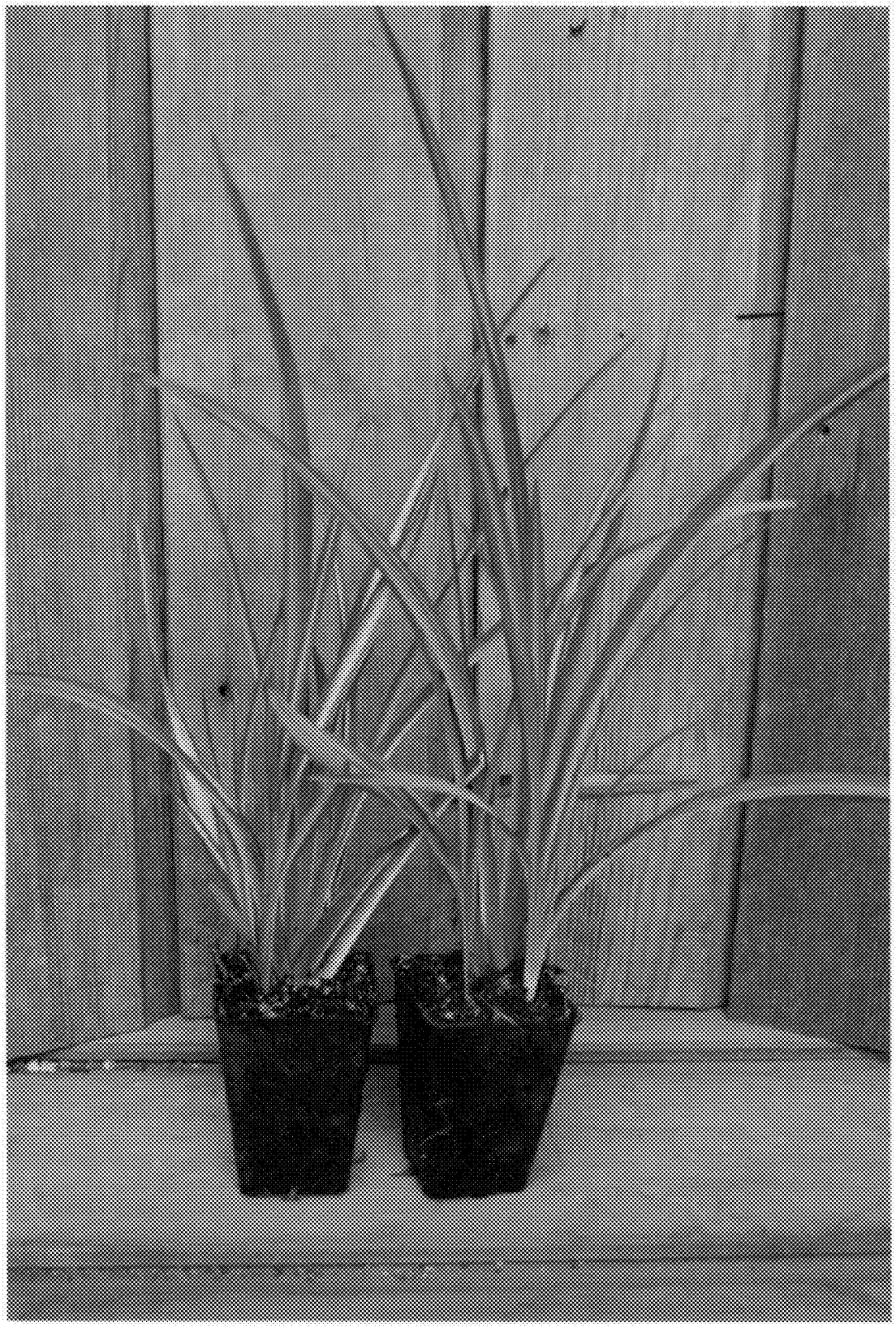
FIG. 1 provides a side view of 'Moonraker'.
Figure 2:
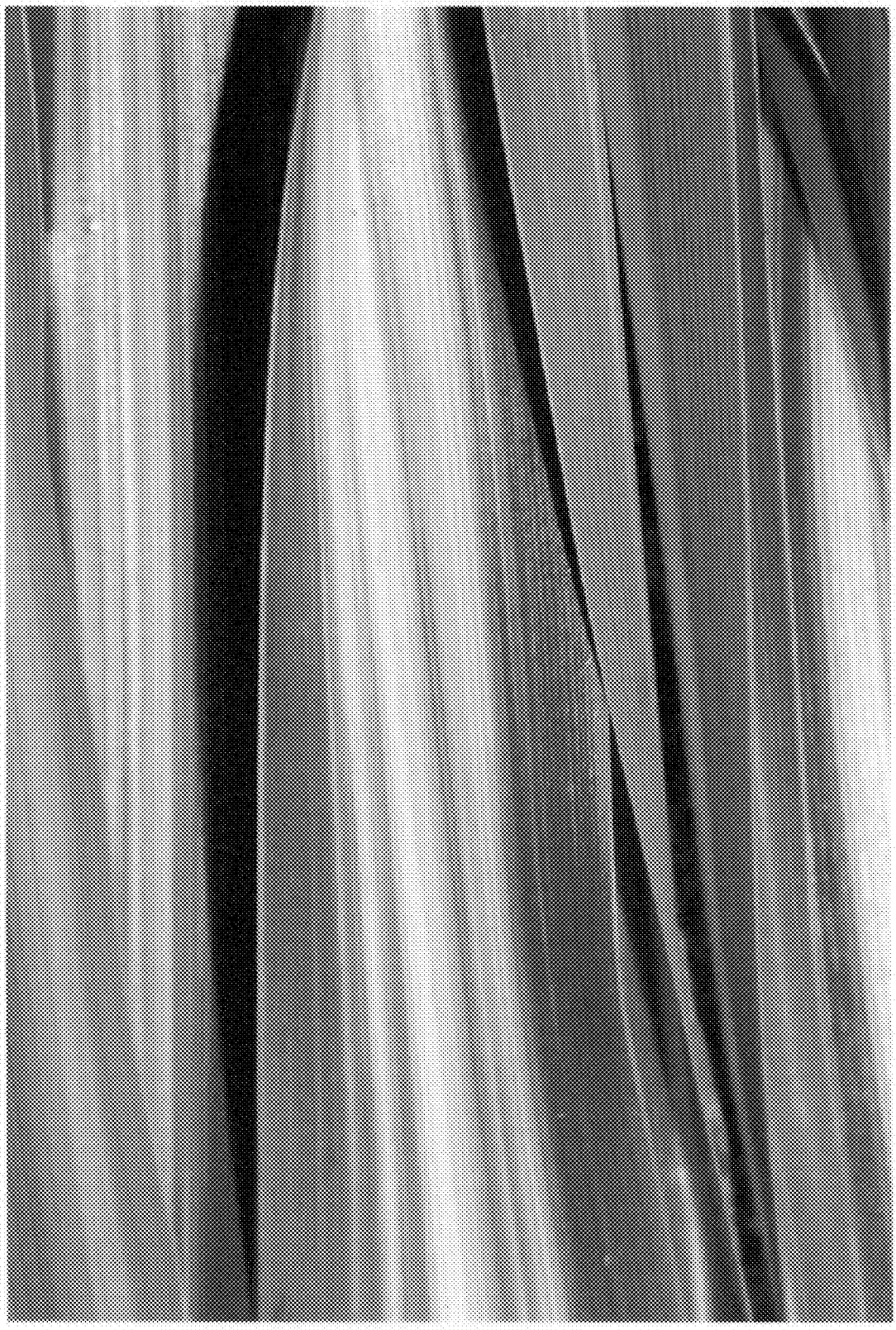
FIG. 2 provides a close up view of the foliage of 'Moonraker'. The colors in the photographs may differ slightly from the color values cited in the detailed botanical description, which accurately describe the colors of the new *Phormium.*

The following is a detailed description of two year-old plants of the new cultivar as grown outdoors in 3-liter containers in Auckland, New Zealand. The plants were grown under average day temperatures of 20° to 27° C. and average night temperatures of 12° to 20° C. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—No flower production has been observed.

*Plant type.*—Perennial, evergreen.

*Plant habit.*—Clump-forming, compact, upright and arching.

*Height and spread.*—Reaches 40 to 60 cm in height and 60 to 70 cm in width when in the landscape.

*Hardiness.*—U.S.D.A. Zones 9a to 10b, tolerant to high temperatures of 40° C. and low temperatures of −5° C.

*Diseases and pests.*—No unique susceptibility or resistance to diseases or pests has been observed.

*Root description.*—Fibrous with some larger fleshy roots, 2 to 4 mm in diameter, vigorous, 8D in color.

*Propagation.*—Division.

*Growth rate.*—Moderate to vigorous relative to *Phormium* with good fan production (4 to 8 fans in a 3-liter container).

*Root development.*—Divisions take 6 to 8 weeks to develop new roots when grown at 20° C.

*Stem description.*—Stem-less, leaves are equitant from base.

Foliage description:

*Leaf shape.*—Lanceolate.

*Leaf division.*—Simple.

*Leaf base.*—Sheathed, overlapping.

*Leaf apex.*—Acuminate.

*Leaf venation.*—Parallel, not prominent, same color as leaves, mid rib protruding on lower surface.

*Leaf margins.*—Entire.

*Leaf attachment.*—Sheathed, lacks petioles.

*Leaf arrangement.*—Equitant.

*Leaf number.*—Average of 20 as grown in a 3-liter container.

*Leaf orientation.*—Held upright and becomes arching, moderately concave with medium to sharp keel.

*Leaf substance.*—Stiff, leathery, durable.

*Leaf surface.*—Smooth with fine longitudinal lines, upper surface satiny, lower surface slightly glaucous.

*Leaf color.*—Young and mature leaves upper surface; centers: 4B to 4D with a occasional thin lines of 146B to 146D, margins: 146A to 147A.

*Leaf size.*—25 to 50 cm in length and 2.5 to 4 cm in width.

It is claimed:

1. A new and distinct cultivar of *Phormium* plant named 'Moonraker' as herein illustrated and described.

* * * * *